United States Patent
Clark et al.

[11] Patent Number: 5,928,160
[45] Date of Patent: Jul. 27, 1999

[54] HOME HEARING TEST SYSTEM AND METHOD

[76] Inventors: Richard L. Clark, 2112 Westover Ter., Burlington, N.C. 27215; David Navone, 3434 Paragon Ave., Stockton, Calif. 95210; Charles Watson, 4104 S. Gran Haven Dr.; Diane Kewley-Port, 2619 Popler Dr., both of Bloomington, Ind. 47401; Howard Hoyt, 302 Brandywine Rd., Chapel Hill, N.C. 27516; Carl V. Miller, 33434 Paragon Ave., Stockton, Calif. 95210

[21] Appl. No.: 08/739,848
[22] Filed: Oct. 30, 1996
[51] Int. Cl.⁶ .................................................. A61B 5/00
[52] U.S. Cl. ................................. 600/559; 73/585
[58] Field of Search ................................. 600/559; 73/585

*Primary Examiner*—Max Hindenburg
*Assistant Examiner*—Charles Marmor, II
*Attorney, Agent, or Firm*—Ostrolenk, Faber, Gerb & Soffen, LLP

[57] ABSTRACT

A home hearing test for use with a conventional home audio system comprising an audio player and a set of headphones connected to the audio player. The home hearing test includes an audio medium such as a compact disc playable in the audio player and containing a calibration tone recorded at a predetermined decibel level and a number of prerecorded sequences of tones. Each sequence has tones recorded at different decibel levels and decreasing by a step value. In a first sequence for obtaining a rough estimation of hearing threshold level, the tones start at 70 dB HL and decrease by 10 dB steps to 0 dB HL. In secondary sequences, tones start and end with tones from the first sequence and decrease in 2 dB steps. The home hearing system includes a calibration device for calibrating the output of the audio system to the ears of a person wearing the headphones against the predetermined decibel level of the calibration tone.

23 Claims, 8 Drawing Sheets

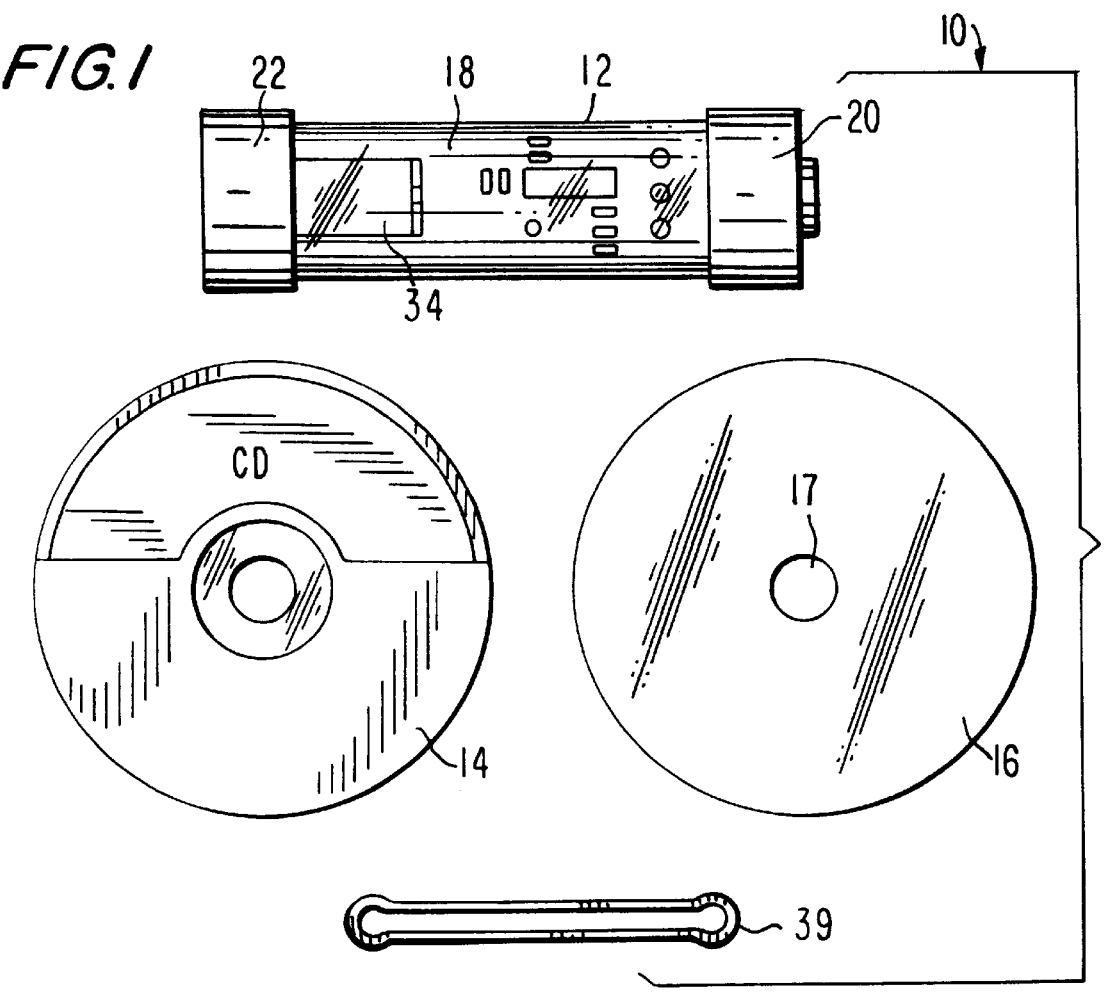
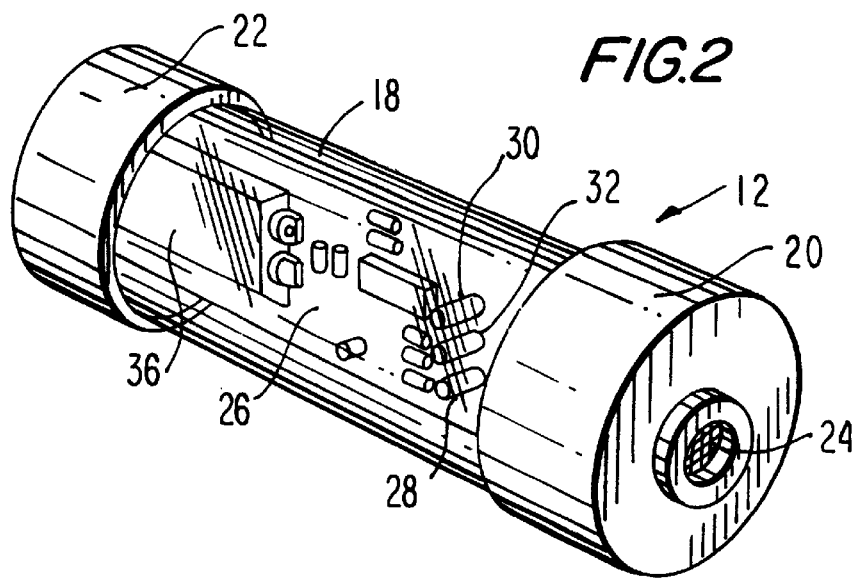

STIMULI FOR BASIC 10dB STEP TEST

| HL | 250Hz | 500Hz | 1000Hz | 2000Hz | 4000Hz |
|---|---|---|---|---|---|
| 70 | | D90<br>SPL81.5 | D85.5<br>SPL77 | D87.5<br>SPL79 | D88<br>SPL79.5 |
| 60 | | D80<br>SPL71.5 | D75.5<br>SPL67 | D77.5<br>SPL69 | D78<br>SPL69.5 |
| 50 | D84<br>SPL75.5 | D70<br>SPL61.5 | D65.5<br>SPL57 | D67.5<br>SPL59 | D68<br>SPL59.5 |
| 40 | D74<br>SPL65.5 | D60<br>SPL51.5 | D55.5<br>SPL47 | D57.5<br>SPL49 | D58<br>SPL49.5 |
| 30 | D64<br>SPL55.5 | D50<br>SPL41.5 | D45.5<br>SPL37 | D47.5<br>SPL39 | D48<br>SPL39.5 |
| 20 | D54<br>SPL45.5 | D40<br>SPL31.5 | D35.5<br>SPL27 | D37.5<br>SPL29 | D38<br>SPL29.5 |
| 10 | D44<br>SPL35.5 | D30<br>SPL21.5 | D25.5<br>SPL17 | D27.5<br>SPL19 | D28<br>SPL19.5 |
| 0 | D34<br>SPL25.5 | D20<br>SPL11.5 | D15.5<br>SPL7 | D17.5<br>SPL9 | D18<br>SPL9.5 |

*FIG.9A*

STIMULI FOR SUPPLEMENTAL 2dB - STEP TESTS
STEP 1: LOSS BETWEEN 60 AND 50 dB HL

| | | | | | |
|---|---|---|---|---|---|
| 60 | ——— | D80<br>SPL71.5 | D75.5<br>SPL67 | D77.5<br>SPL69 | D78<br>SPL69.5 |
| 58 | ——— | D78<br>SPL69.5 | D73.5<br>SPL65 | D75.5<br>SPL67 | D76<br>SPL67.5 |
| 56 | ——— | D76<br>SPL67.5 | D71.5<br>SPL63 | D73.5<br>SPL65 | D74<br>SPL65.5 |
| 54 | ——— | D74<br>SPL65.5 | D69.5<br>SPL61 | D71.5<br>SPL63 | D72<br>SPL63.5 |
| 52 | ——— | D72<br>SPL63.5 | D67.5<br>SPL59 | D69.5<br>SPL61 | D70<br>SPL61.5 |
| 50 | ——— | D70<br>SPL61.5 | D65.5<br>SPL57 | D67.5<br>SPL59 | D68<br>SPL59.5 |
| 48 | ——— | D68<br>SPL59.5 | D63.5<br>SPL55 | D65.5<br>SPL57 | D66<br>SPL57.5 |
| 46 | ——— | D66<br>SPL57.5 | D61.5<br>SPL53 | D63.5<br>SPL55 | D64<br>SPL55.5 |
| 44 | ——— | D64<br>SPL55.5 | D59.5<br>SPL51 | D61.5<br>SPL53 | D62<br>SPL53.5 |
| 42 | ——— | D62<br>SPL53.5 | D57.5<br>SPL49 | D59.5<br>SPL51 | D60<br>SPL51.5 |
| 40 | ——— | D60<br>SPL51.5 | D55.5<br>SPL47 | D57.5<br>SPL47 | D58<br>SPL49.5 |
| HL | 250Hz | 500Hz | 1000Hz | 2000Hz | 4000Hz |

*FIG. 9B*

HOME HEARING TEST SYSTEM AND METHOD

COPYRIGHT NOTICE

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

The invention disclosed herein relates to the field of audiology. In particular, the present invention relates to a system and method for allowing people to test their hearing at home using conventional, commercially available audio systems such as compact disk players and headphones, and to a device for calibrating the level of the sounds presented to the headphones against a calibration tone of a predetermined decibel level.

Although audiometric equipment exists for testing hearing, the primary elements being audiometers (such as pure tone, speech, manual, automatic, etc.) and earphones, it is generally expensive and complex. As a result, audiometric equipment is generally available only in specialized audiometry clinics, and trained audiologists are required to operate the equipment, administer the tests, and evaluate the results. Additional information regarding existing audiometers and the procedures for accomplishing diagnostic hearing threshold measurement is available, among other places, in Davis, H. and Silverman, S. R., *Hearing and Deafness*, Chapter 7 (Holt, Rinehart and Winston 1970), American Speech-Language-Hearing Association ("ASHA") Guidelines for Manual Pure-Tone Threshold Audiometry (1977), and American National Standard Institute ("ANSI") Specification for Audiometers (1989), each of which is hereby incorporated by reference into this application as background information.

Because audiometric equipment is generally available only in clinics, it is widely believed that as many as 80% of the approximately 22 million people who suffer from hearing loss in the U.S. have not had their hearing tested. Many people are reluctant to visit hearing clinics for a hearing test for several reasons, including the cost of the test, the time and inconvenience involved in scheduling an appointment and waiting for and undergoing the test, and privacy concerns.

Perhaps more importantly, hearing loss is often a gradual process which allows people time to adjust to their hearing loss without noticing any significant difference in their hearing capabilities. As a result, many people with hearing loss do not notice their hearing loss and are not aware of any need to have their hearing tested.

Given the widely recognized importance of good hearing and the prevalence of hearing impairment, there is a need for an inexpensive hearing test which would allow people to easily detect hearing loss and thus determine whether they should seek further testing or assistance. Just as thermometers and blood-pressure monitoring devices increase awareness and help people determine when they have a medical problem that needs attention, there is a need for a hearing test which people can administer in their homes and which would increase awareness about hearing and allow people to determine whether they or their family members have a hearing problem that should be evaluated by an audiologist.

Attempts have been made to do hearing screening by telephone, screening being, as compared to monitoring or diagnostic audiometry, a limited, simplified, pass-fail type test employing a tone at a single frequency. See, for example, Frank, T., *Is telephone hearing screening a valid concept?* The Hearing Journal, 42, 26–31 (1989); and Gardner, H, *Rebuttal to the ASHA Committee Position Paper on telephone hearing screening testing*, The Hearing Journal, 42, 31 (1989). Frank, 1989; Gardner, 1989). However, the problems in controlling the level and spectral quality of stimuli presented over telephone equipment have been serious enough to lead ASHA to the conclusion that "telephone hearing screening should be viewed with caution until its validity and efficacy are demonstrated" ASHA, *Telephone hearing screening*, Asha, 30, 53 (1988a, December).

Thus, there remains an unfilled need for a system and method for allowing people to test their hearing at home. To be effective and available to a wide range of people, the test should be usable with most conventional, commercially available audio equipment people have in their homes, such as audio players, personal computers, and headphones. In addition, the test should be inexpensive, accurate, and easy to use, administer, and score. The present invention provides a system and method having these and other advantages.

SUMMARY OF THE INVENTION

It is an object of the present invention to detect hearing loss.

It is another object of the present invention to provide an inexpensive and accurate system for testing human hearing using a home audio system.

It is another object of the present invention to provide a reusable system and repeatable method for testing human hearing which is simple and easy to administer and score.

It is another object of the present invention to provide a compact-disk-based home hearing test which can be used with a wide variety of headphones.

It is another object of the present invention to provide a home hearing test in which digital signals are transmitted to a person's home over a computer network such as the global Internet and are converted to audio signals at the person's home using commercially available computer hardware and software.

It is another object of the present invention to provide a hearing test which may be administered by people untrained in audiology.

It is another object of the present invention to provide a device for calibrating the sound pressure levels produced by a home audio system including an audio player and a set of headphones.

The above and other objects are achieved by a home hearing test system for use with an audio system comprising an audio player and a sound reproducer such as speakers or headphones connected to the audio player. The home hearing test system comprises an audio medium containing signals recorded thereon which are playable by the audio player, the signals comprising at least one calibration tone recorded at a predetermined decibel level and one or more prerecorded sequences of tones, each sequence having tones at different decibel levels, and a calibration device for calibrating the output of the audio system to the ears of a person listening to the output of the sound reproducer against the predetermined decibel level of one of the calibration tone(s). The calibration device, in other words, adjusts the output of the system through the sound reproducer based on the calibration tone to provide the one or more prerecorded sequences of tones at predetermined decibel levels to the ears of a person.

In preferred embodiments, the audio medium is a digital audio source having a highly accurate digital playback in order to provide tones having decibel levels which are accurate once the audio system is calibrated with the calibration tone. For example, the audio medium may comprises a compact disc ("CD"), CD-ROM, digital cassette, digital versatile disc, or other digital medium. The audio system then comprises an appropriate audio player which is capable of playing the digital medium, such as a conventional, commercially available CD player, a cassette player, or a CD-ROM player and sound card connected to a personal computer. Alternatively, the audio medium may be situated at a server computer connected to a network such as an intranet, a subscriber-based network, or the global Internet, and the audio medium comprises a client computer connected to the network for receiving digital signals from the server and converting the signals to audio through the use of a sound card or the like.

In preferred embodiments, the audio medium contains recorded thereon several sequences of pure tones used in testing a person's hearing. In a first sequence of tones, the decibel levels of the tones decrease or increase by a first step value such as 10 dB, ranging from a maximum dB HL to a minimum dB HL. "HL" refers to Hearing Level or Hearing-threshold Level, meaning generally the number of decibels that a person's threshold of hearing lies above a standard hearing reference zero which represents an audiometric normal for a pure tone audiogram. Zero dB HL is usually the lowest decibel level tone presented during a hearing test. Hearing Level is distinguished from sound pressure level, or "SPL", a logarithmic scale having a zero reference level at a pressure of 0.0002 dyne/cm$^2$.

In one or more other sequences of tones recorded on the audio medium, the decibel levels of the tones decrease or increase by a second step value, the first step value being different than the second step value. In preferred embodiments, the first step value is 10 dB and the second step value is 2 dB.

In further embodiments, the audio medium contains a plurality of secondary sequences of tones which decrease by the second step value, each of which begins at a starting tone having a decibel level equal to the decibel level of one of the tones in the first sequence and ends at an ending tone having a decibel level equal to the decibel level of another of the tones in the first sequence. Usually, the secondary sequences begin and end at decibel levels of a pair of consecutive tones in the first sequence. For example, if the first sequence begins at 70 dB HL and decreases by 10 dB steps to 0 dB HL, the plurality of secondary sequences include a sequence staring at 60 dB HL and decreasing by 2 dB steps to 50 dB HL, a sequence starting at 50 dB HL and decreasing by 2 dB steps to 40 dB HL, etc. In this way, a person can use the first sequence to obtain a rough estimate of their hearing level and can then select, based on the rough estimate, one of the secondary sequences to obtain a more accurate estimation of their hearing level.

When a CD or other digital medium is used having a plurality of tracks or other discrete, selectable units of storage, each of the first and secondary sequences are stored on separate tracks so the person may easily select and play any desired sequence.

The audio medium contains recorded thereon a plurality of tones at each decibel level which differ from one another in frequency. Although any range of frequencies may be provided, to accommodate limitations in current CD and headphone technology the frequencies of the tones preferably range between 250 Hz and 4000 Hz, inclusive.

In preferred embodiments, the sound reproducer is a set of headphones and the calibration device comprises at least one transducer such as a microphone for detecting sound being output by at least one earpiece of the headphones and converting the detected sound into an electrical signal having at least one parameter related to the decibel level of the detected sound, a first circuit coupled to the transducer and having an output related to the relationship between the parameter or parameters of the electrical signal and at least one reference level related to the predetermined decibel level of the calibration tone, and at least one indicator coupled to an output of the first circuit for indicating the relationship between the electrical signal and the reference level or levels.

The first circuit may comprise a reference circuit for producing the reference level or levels and a comparator circuit coupled to receive the electrical signal and the reference level(s). In some embodiments, the calibration device calibrates the audio system to within a window of accuracy, such as ±1 dB audio. The reference circuit produces a first reference level corresponding to a high end of the window of accuracy and a second reference level corresponding to a low end of the window of accuracy. The comparator circuit compares the electrical signal to the first and second reference levels to thereby detect when the electrical signal is between the first and second reference levels. Such a comparator circuit may be implemented as a window comparator which in some embodiments comprises a first comparator coupled to receive as inputs the electrical signal and the first reference level and which outputs a signal when the electrical signal is greater than the first reference level, a second comparator which is coupled to receive as inputs the electrical signal and the second reference level and which outputs a signal when the electrical signal is less than the second reference level, and a decision circuit coupled to the outputs of the first and second comparators which drives the indicator or indicators when neither the first nor second comparator output a signal.

The indicator(s) may comprise one or more light emitting diodes ("LED"s). In some embodiments, the indicator(s) comprises three LEDs—one LED for indicating when the parameter of the electrical signal is substantially below the reference level, a second LED for indicating when the parameter is approximately equal to the reference level, and a third LED for indicating when the parameter is substantially greater than the reference level. When a window comparator as described above is used, the high and low indicating LEDs are coupled to the outputs of the two comparators and the LED indicating an approximately equal condition is coupled to the output of the decision circuit.

To increase the accuracy of the calibration device, the device may include means for providing a first level of contact pressure between the calibration device and at least one earpiece of the headphones which is substantially equal to a second level of contact pressure between the earpiece and an ear when the headphones are worn by a person. The means may comprise a housing for the calibration device having a length approximately equal to the width of an average human head, which is about 6" wide.

The calibration device may include additional elements such as an automatic turn-off circuit for preserving the life of a battery powering the calibration device, an amplifier circuit for amplifying the electrical signal produced by the transducer, a rectifier circuit for producing a DC voltage level from the electrical signal, and a high pass filter circuit coupled to the transducer for minimizing the presence of low frequencies in the electrical signal to thereby minimize background noise present while the system is being used to test a person's hearing.

To make the calibration device compatible with a conventional set of large headphones, such as may have cup earpieces, the home hearing test system may include an earpiece adapter plate releasably connectable to an end of the calibration device and having a surface area substantially commensurate with a surface area of an earpiece of the large headphones.

The above and other objects of the invention are also achieved by a method for testing a person's hearing at the person's home using an audio player, a sound reproducer such as a set of headphones connected to the audio player, and an audio medium playable in the audio player. The method comprises calibrating the output of the headphones against a calibration tone of a predetermined decibel level prerecorded on the audio medium, listening through the headphones to a first sequence of tones prerecorded on the audio medium, the first sequence comprising a plurality of tones recorded at decibel levels which decrease or increase, and indicating which of the tones in the first sequence were heard and/or not heard.

The method may further comprise, based on tones in the first sequence indicated to have been heard and/or not heard, selecting and listening to a second sequence of tones prerecorded on the audio medium, the second sequence having a plurality of tones recorded at different decibel levels ranging between a first tone in the first sequence which was not heard and a second tone in the first sequence which was heard. The tones in the first sequence increase or decrease by a first step value and the tones in the second sequence increase or decrease between the first tone and second tone at a second step value, the second step value being smaller than the first step value.

BRIEF DESCRIPTION OF THE DRAWINGS

The invention is illustrated in the figures of the accompanying drawings which are meant to be exemplary and not limiting, in which like references refer to like or corresponding parts, and in which:

FIG. 1 is shows one embodiment of a home hearing test system of the present invention including a calibrator and CD;

FIG. 2 is a perspective view of one end of the calibrator of FIG. 1;

FIG. 9A is a table showing tones recorded on the CD for a 10 dB-step test in accordance with one embodiment of the present invention;

FIG. 9B is a table showing tones recorded on the CD for a 2 dB-step test in accordance with one embodiment of the present invention.

DETAILED DESCRIPTION OF THE PREFERRED EMBODIMENTS

Figure 3:
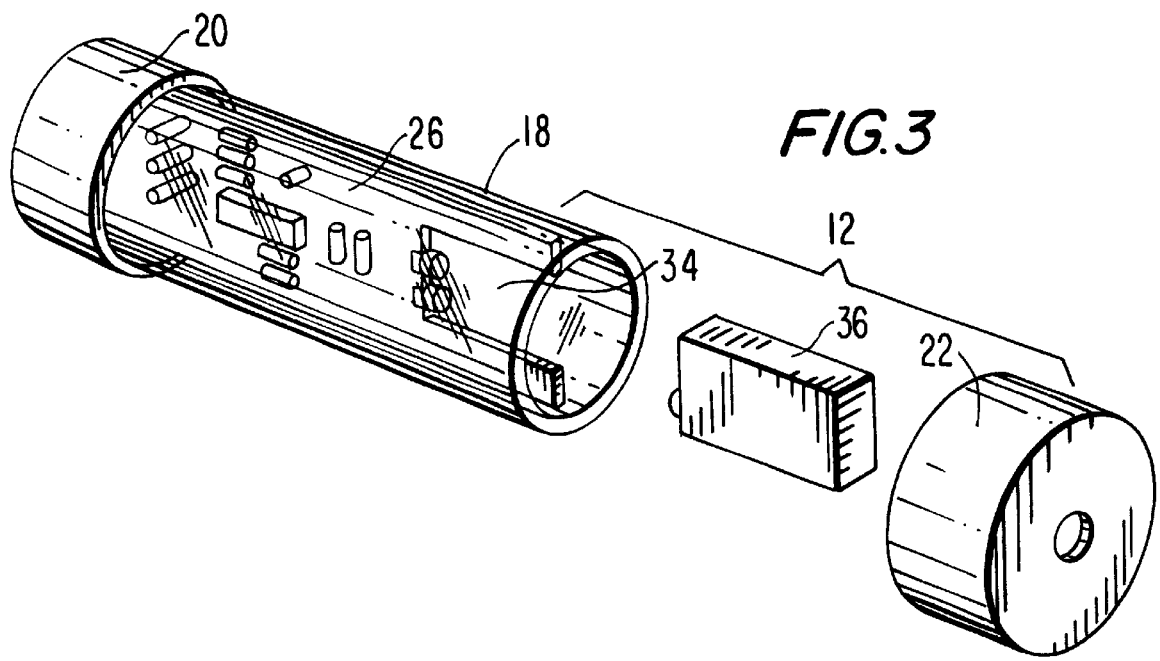
FIG. 3 is a view of the calibrator of FIG. 1 with one end cap removed.

With reference to the drawings in FIGS. 1–7, one preferred embodiment of the home hearing test system 10 of the present invention comprises a calibrator 12, a compact disc ("CD") 14, a plastic disc adapter plate 16, and an elastic band 39. Each element of the system 10, and the method for using the system 10 to perform a hearing test, will be described in detail below.

In some embodiments, the home hearing test 10 is used with a CD player system (not shown) and a set of conventional headphones 2. The CD player system could include a conventional CD player and amplifier or any other audio system with which CD technology is compatible, such as a CD-ROM drive and sound card connected to a personal computer or a system based on a digital versatile disc format developed in combination by Sony Corp., Philips Electronics, Toshiba, Matsushita and others.

Alternatively, the CD or other digital memory medium could be located at a server of a network such as an intranet or the global Internet. The person would connect to the server over the network using a personal computer, would download the digital signals which comprise the hearing test, and would store the signals in a local memory device such as RAM, CD-ROM, or hard disk. The digital signals would then be converted to audio signals through the use of a sound card connected to the personal computer. The calibrator 12 and associated equipment would be used to calibrate the headphones as described herein. In this case, a person would not need to have physical possession of the CD or other memory device, and the test could be updated remotely at the server without the need to provide a new memory device to the person.

Any conventional set of headphones may be used, such as those available from Sony, Sennheiser, Philips, Magnavox, Zenith, Labtec, or many other sources, with headphones having a flat frequency response (within a 3 dB SPL window) being preferred for more accurate results.

As described further below, the CD contains prerecorded thereon a 1 kHz, 77 dB SPL calibration tone for calibrating the audio system, as well as tones, instructions, and/or other content such as speech which constitutes the hearing test(s).

Figure 4:
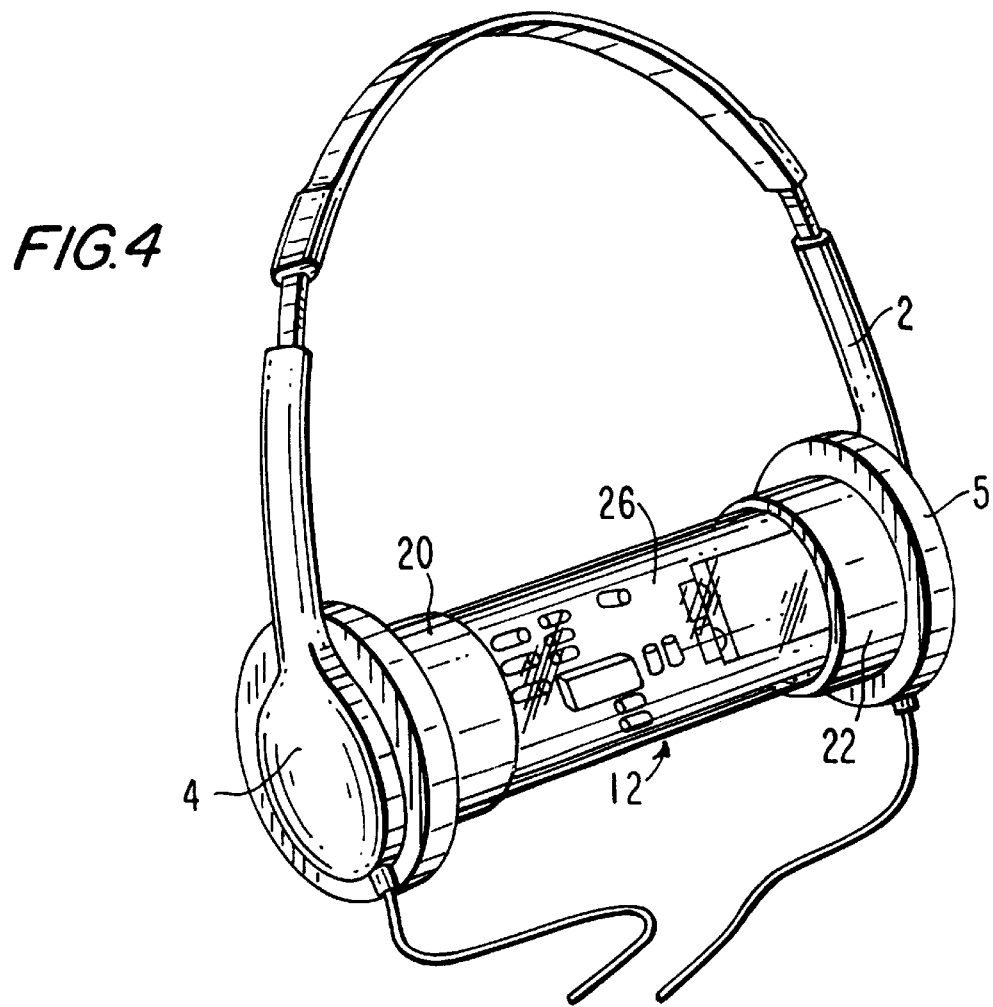
FIG. 4 is a perspective view of the calibrator of FIG. 1 with a set of headphones positioned around the calibrator.

In preferred embodiments, the calibrator 12 consists of a Plexiglas housing tube 18 having plastic end caps 20 and 22 on either end thereof. The housing tube 18 houses a small condenser microphone 24 (FIG. 2) which is slightly recessed into the plastic cap 20 on one end of the tube 18. In preferred embodiments, the microphone 24 is a Panasonic model WM-54 BT microphone. As shown in FIG. 4, during calibration of the audio system one earpiece 4 of a set of headphones 2 is placed over the end cap 20 into which the microphone 24 is recessed, so that the earpiece 4 is in close proximity with the microphone 24 and the output of the earpiece 4 is received by the microphone 24 with minimal distortion or interference.

The calibrator 12 is 1.75" in diameter by 6" long. The length of the calibrator 12 is thus approximately equal to the width of an average human head. This facilitates placement of the calibrator 12 between the earpieces 4, 5 of the headphones 2 (FIG. 4) such that the earpieces 4, 5 provide substantially the same contact pressure on the end caps 20 and 22 as they would on the average human ear, thus simulating the coupling between the earphone 4 and a human ear.

The calibrator 12 may alternatively contain two microphones, one on either side thereof. However, the use of a single microphone 24 is preferred because there is no need to calibrate both earpieces 4, 5 of a set of headphones 2. Rather, the person taking the hearing test can test one ear first through the calibrated earpiece, then turn the headphones 2 around to test the other ear using the same calibrated earpiece. In addition, calibrating both earpieces 4, 5 simultaneously is difficult due to variations between the earpieces 4, 5 which increase the difficulty in matching the outputs of both earpieces 4, 5 to a single calibration tone.

The calibrator 12 also contains within the housing 18 threshold detection circuitry 26 (described in detail below in reference to FIG. 8) coupled to the output of the microphone 24. The threshold detection circuitry 26 receives an electrical signal output by the microphone 24 and compares the signal to two reference voltages which correspond to high and low ends of a window of calibration accuracy, which in one preferred embodiment is about ±1 dB of the 77 dB SPL calibration tone.

The results of these comparisons are output to three colored light emitting diodes ("LED"s)—a yellow LED 28, green LED 30, and red LED 32. The three indicator LEDs provide feedback for the level adjustment during calibration. As the person performing the calibration adjusts the volume on the audio system, one of the three LEDs is lit—the yellow LED 28 indicates a volume signal level that is more than 1 dB below the threshold of the window, the green light 30 indicates that the signal level is within the desired 2 dB (±1 dB) window, and the red LED 32 indicates that the signal level has exceeded the upper threshold of the window by over 1 dB. As one skilled in the art will recognize, alternative indicators may be used, including a digital LCD readout, a continuous meter, an audio indicator, etc., to display the signal level during calibration.

The housing 18 contains a cavity 34 for the placement of a 9-volt battery 36 (FIG. 3) which powers the calibrator 12. The end cap 22 is removable from the housing 18 (see FIG. 3) for placement of the battery 36 within the cavity 34. As described below, in preferred embodiments the calibrator 12 contains an automatic turn-off circuit 48 to minimize unnecessary power drainage of the battery 36 when the calibrator 12 is not in use.

Figure 5:
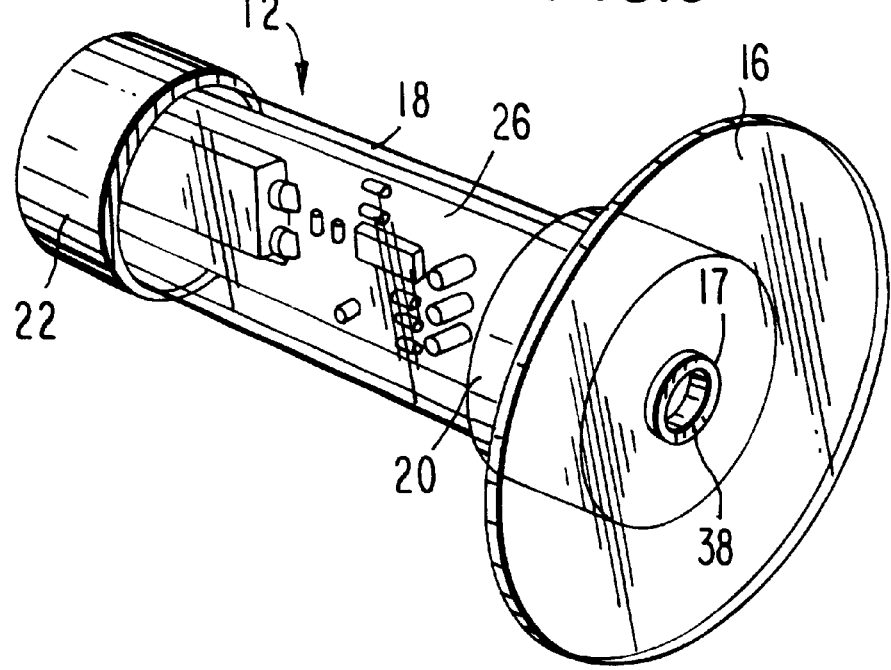
FIG. 5 is a perspective view of the calibrator of FIG. 1 with a disc adapter plate installed on one end.
Figure 6:
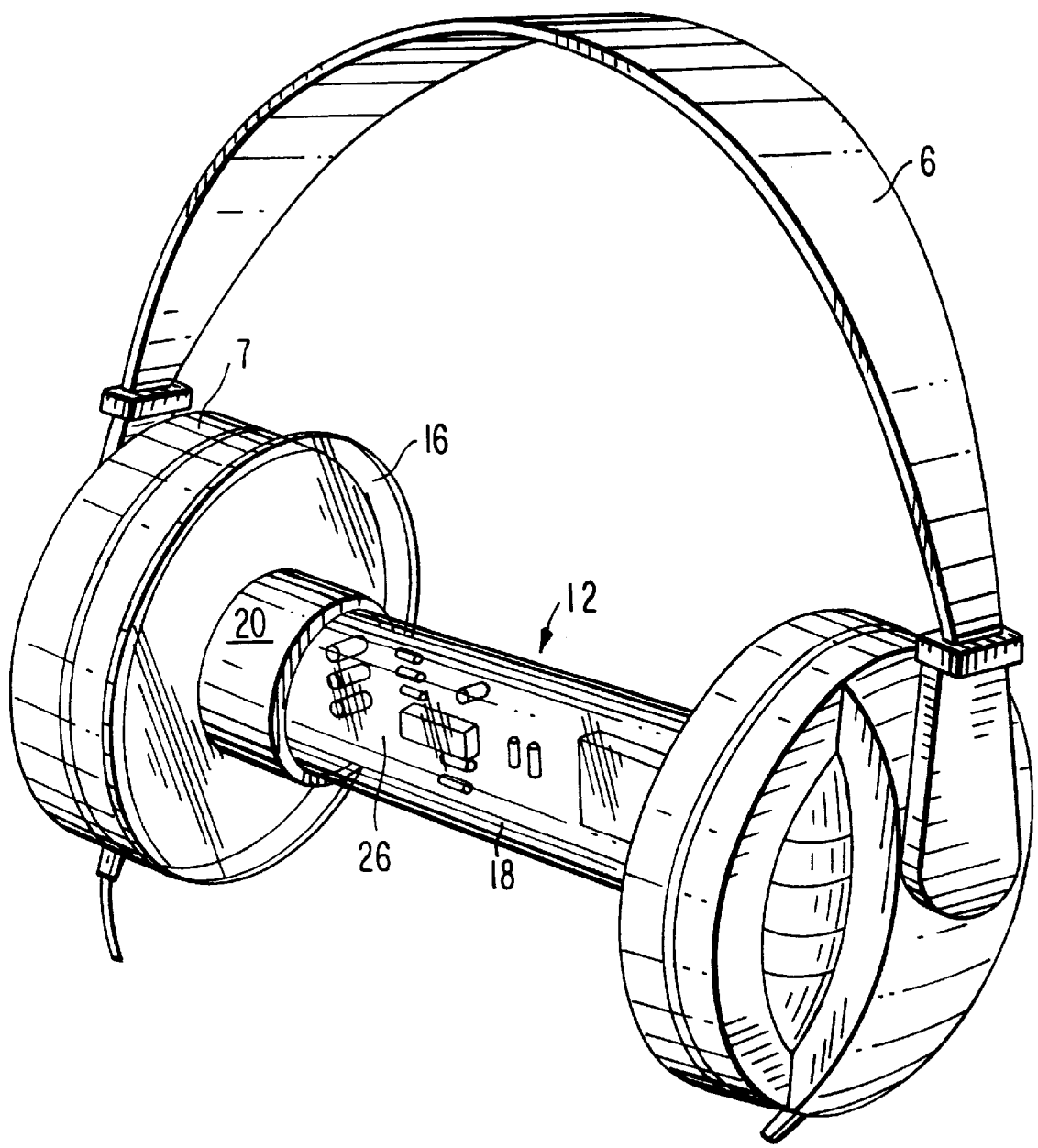
FIG. 6 is a perspective view of the calibrator with a disc adapter plate installed thereon as in FIG. 5 and with a set of headphones positioned around the calibrator.

A good seal between the end cap 20 and the earpiece 4 can be obtained with a wide variety of headphones 2. However, some larger types of headphones, sometimes referred to as full size or circumaural headphones, such as model HD25 and HD265 headphones available from Sennheiser or model LT-8xx headphones from LabTec, have cup earpieces with large surface areas which may not balance well on the end cap 20. As shown in FIGS. 5 and 6, the plastic disc adapter plate 16, having a surface area approximately equal to the surface area of an average large set of headphones 6, is used to help balance the large headphone earpiece 7 placed in close proximity with the end cap 20 having the microphone 24 recessed therein. The adapter plate 16 is releasably connectable to the end cap 20 by virtue of a hole 17 in the adapter plate 24 which is sized to encompass a ring 38 protruding from the central area of the end cap 20. The pressure from earpiece 7 helps retain the adapter plate 16 on the end cap 20 while the headphones 6 are being calibrated.

Alternatively, the hole 17 and ring 38 can be sized to engage tightly. One skilled in the art will recognize that many alternative structures may be employed to releasably connect the adapter plate 16 to the end cap 20, including clips, adhesive, Velcro strips, etc.

Figure 7:
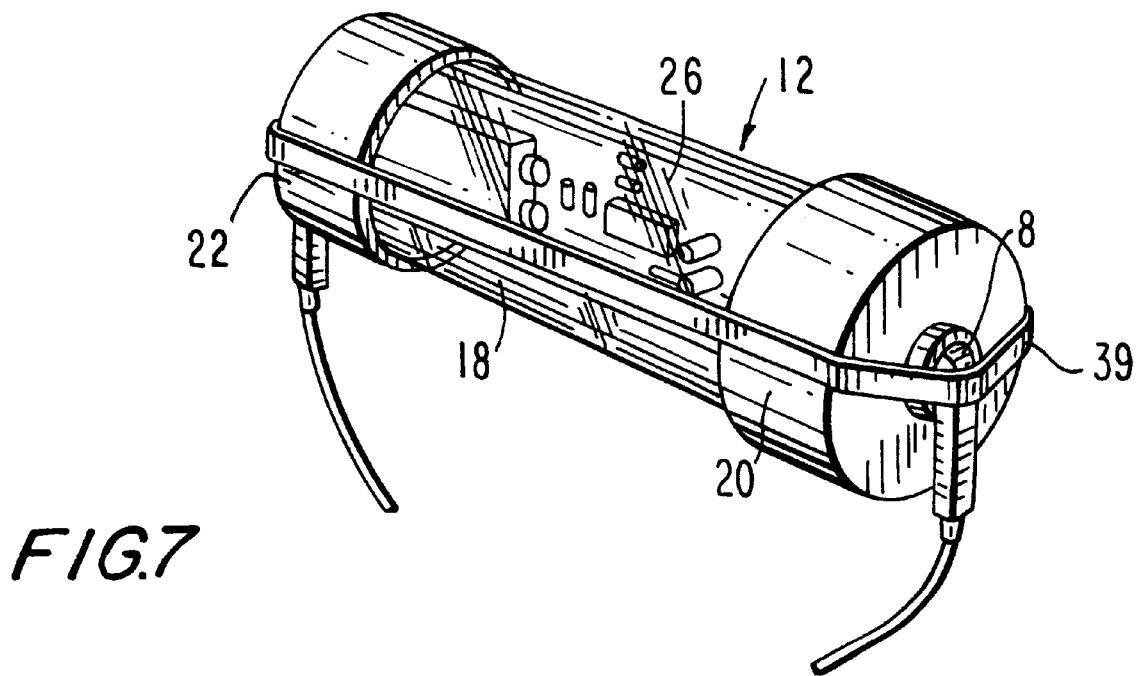
FIG. 7 is a perspective view of one end of the calibrator of FIG. 1 with an ear bud on a set of headphones positioned at one end.

Other types of headphone sets, such as model LT-2xx headphones from LabTec, contain earbuds. As shown in FIG. 7, the earbud 8 of such a headphone set is placed within or on the ring 38 and held in place by an elastic band 39 placed lengthwise around the calibrator 12.

Figure 8:
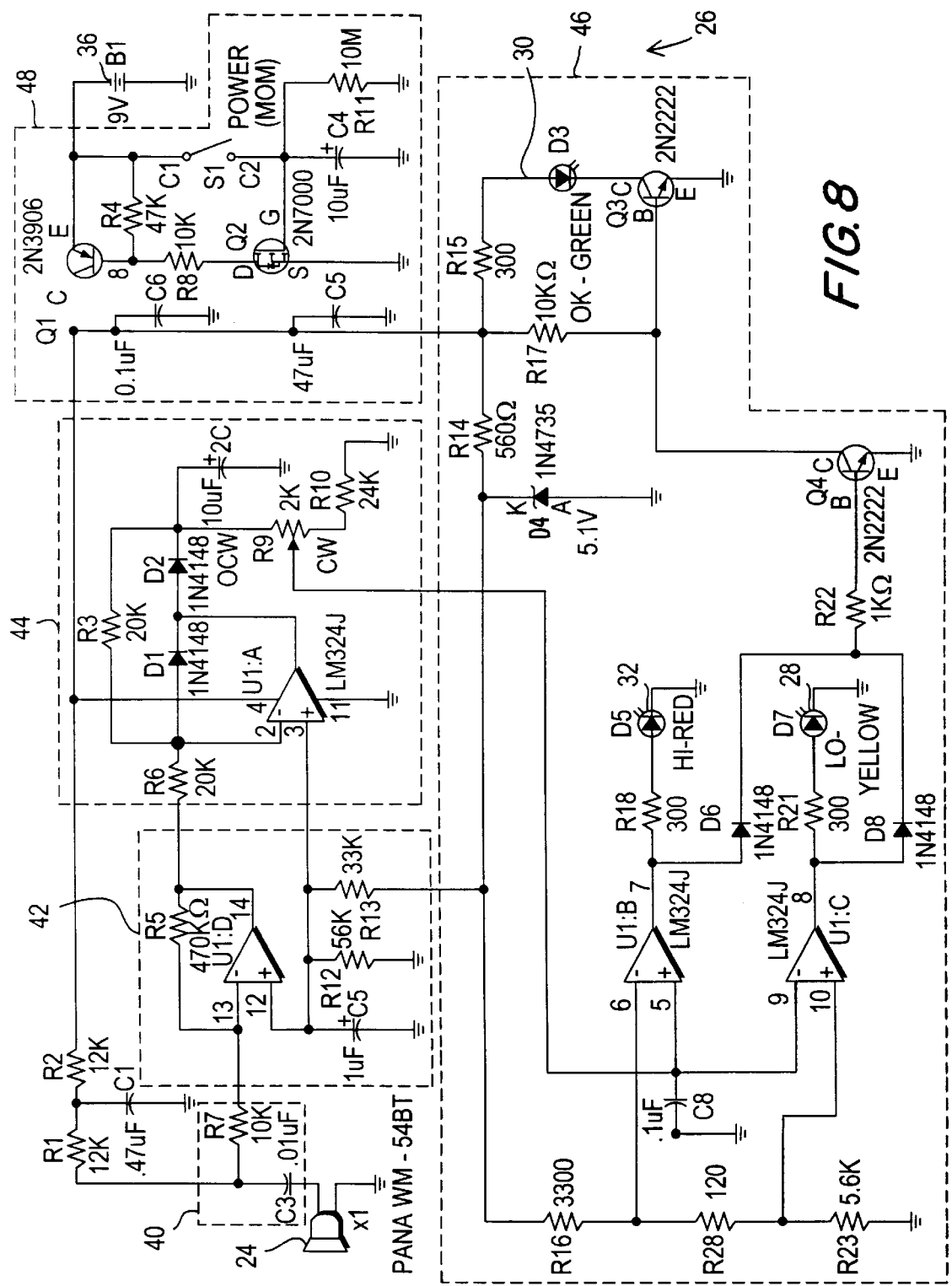
FIG. 8 is a circuit schematic of one embodiment of the calibrator.

As shown in the circuit schematic of FIG. 8, the main elements of the threshold detection circuit 26 are a high pass filter 40, a pre-amplifier circuit 42, a half wave rectifier circuit 44, a window comparator circuit 46, and an automatic turn-off circuit 48 coupled to the 9 volt battery 36 which supplies power to the threshold detection circuit 26. Each element is described in turn.

The high pass filter 40 is coupled to the output of the microphone 24 and contains a 0.01 $\mu$F capacitor C3 and 10k$\Omega$ resistor R7. The microphone 24 outputs an AC electrical signal having a peak amplitude dependent upon the decibel level of the sound detected by the microphone. The high pass filter passes with little or no attenuation signal frequencies above about 500 Hz, and progressively blocks lower signal frequency components output by the microphone 24 which often result from room and other background noise which could adversely affect proper calibration.

The output of the high pass filter 40 is coupled to the input of the high gain pre-amplifier 42 consisting of op amp U1:D (one of four op amps on a model LM324J quad op amp IC) and a 470k$\Omega$ resistor R5 in the feedback path to the inverting input. The noninverting input of the op amp U1:D is grounded through an RC circuit consisting of a 1 $\mu$F capacitor C5 connected in parallel with a 56k$\Omega$ resistor R12. The high gain pre-amplifier has a gain of 40 dB.

The AC voltage output of the pre-amplifier circuit 42 is coupled to the input of the halfwave rectifier circuit 44, which rectifies the AC electrical signal and outputs a DC voltage level proportional to the peak incoming AC voltage. The rectifier circuit 44 includes a 20k$\Omega$ input resistor R6 and op amp U1:A. A first feedback path is operational during the positive going portions of the AC input voltage. When the input voltage becomes positive on the inverting input pin 2 of U1:A relative to the voltage on pin 3 of U1:A, an inverted negative voltage appears on the output pin 1 of U1:A, forward biasing a 1N4148 diode D1, and clamping the output pin 1 voltage to −0.6 volts relative to reference pin 3. When the input voltage becomes negative on inverting input pin 2 of U1:A, the output pin 1 becomes positive, forward biasing a 1N4148 diode D2, and closing the feedback loop through 20k$\Omega$ resistor R3 to pin 2. At this point the stage operates as a unity gain inverter, and will charge 10 $\mu$F capacitor C2 to the peak negative value of the incoming AC voltage.

The non inverting input pin 3 of op amp U1:A is held at an AC ground potential by bypass 1 $\mu$F capacitor C5. Pin 3 is biased positive relative to ground (for bipolar operation from a single power supply) by the voltage divider formed by 33k$\Omega$ resistor R13 and 56k$\Omega$ resistor R12. The positive end of this voltage divider is fed by the regulated reference voltage at the 5.1 volt Zener diode D4. This ensures that the DC operation of both the pre-amplifier stage formed by U1:D and it's associated circuitry and the half wave rectifier stage formed by U1:A and it's circuitry are stable as both temperature and battery voltage change.

As a result of this configuration, the electrical signal is clamped when the voltage at the inverting input of the op amp is positive, and is equal to the absolute value of the input voltage when the input voltage is negative. An RC filter circuit consisting of variable resistor R9, fixed resistor R10, and 10 $\mu$F capacitor C2 minimizes the ripple in the output voltage. The variable resistor R9 is used to calibrate the threshold detection circuit 26 during manufacture.

Aside from powering the pre-amplifier circuit 42 and the rectifier circuit 44, the power from the battery 36 is also utilized to supply reference voltage levels to which the electrical signal is compared. The power supplied for the reference voltage levels is regulated by a 5.1V zener diode D4. The desired voltage reference levels are established by a voltage divider consisting of 3.3k$\Omega$ resistor R16, 120$\Omega$ resistor R20 and 5.6k$\Omega$ resistor R23 arranged in series. The two reference voltages are supplied as the high and low voltages to the window comparator circuit 46, the high and low voltages representing the high and low ends of the desired window of calibration accuracy. As one skilled in the art will recognize, the relative resistance values in the voltage divider are chosen to provide the proper window.

The window comparator circuit 46 functions as follows. The high voltage reference level is coupled to the inverting input of a first comparator U1:B and the low voltage reference level is coupled to the noninverting input of a second comparator U1:C. The electrical signal received from the half-wave rectifier circuit 44 is coupled to the other inputs of the comparators, i.e., the noninverting input of the comparator U1:B and the inverting input of the comparator U1:C. If the electrical signal has an amplitude higher than the high voltage reference level, the output of comparator U1:B is high, turning on the red LED 32, and the output of comparator U1:C is low. If the amplitude of the electrical signal is lower than the low voltage reference level, the output of comparator U1:C is high, turning on yellow LED 28, and the output of comparator U1:B is low.

A 2N2222 transistor Q4 is coupled at its base to the outputs of both comparators through 1N4148 diodes D6 and D8. Another 2N2222 transistor Q3 is coupled at its base to the collector of transistor Q4, and the collector of transistor Q3 is coupled to the green LED 30. When the output of either comparator is high, the transistor Q4 is turned on and becomes saturated, thus producing a low voltage output which fails to turn on transistor Q3. In that case, the green LED 30 is off. When the outputs of both comparators are low, which occurs when the amplitude of the electrical signal is lower than the high voltage reference level but higher than the low voltage reference level, the transistor Q4 is nonconducting, biased off, producing a high voltage at the base of transistor Q3 which turns it on, thereby supplying current to the green LED 30 to turn it on.

As a result, the window comparator circuit 46 provides that the red LED 32 goes on only when the decibel level of the sound from which the electrical signal is generated is higher than the high end of the window, the yellow LED 28 goes on only when the sound's decibel level is lower than the low end of the window, and the green LED 30 goes on only when the decibel level is within the window.

The automatic turn-off circuit 48 comprises a normally open, momentary on push button switch S1 coupled to the battery 36, a 10 $\mu$F capacitor C4 coupled to switch S1, a 10M$\Omega$ resistor R11 arranged in parallel with capacitor C4, a 2N7000 MOS FET Q2 coupled to the capacitor C4, and a 2N3906 transistor Q1 coupled at its base to MOS FET Q2 through a 10k$\Omega$ bias resistor R8.

The automatic turn-off circuit 48 functions as follows. In the quiescent state, the battery 36 voltage is applied to the emitter of the transistor Q1. The bias resistor R4 holds transistor Q1 in the cut-off mode so that no power is applied to the threshold detection circuit 26. When the push button switch S1 is pressed, capacitor C4 is almost immediately charged up to the voltage of the battery 36. The positive voltage on capacitor C4 places a forward bias on the gate on the MOS FET Q2 which causes it to saturate and draw current through the emitter-base junction of transistor Q1 and resistor R8. This action alters the bias on the transistor Q1 and causes it to conduct, thereby supplying current to the threshold detection circuit 26. Current from the battery continues to pass through transistor Q1 to the threshold detection circuit 26, and transistors Q1 and Q2 remain in this state, while capacitor C4 discharges through resistor R11.

As capacitor C4 discharges and approaches zero volts, the MOS FET Q2 no longer conducts and transistor Q1 returns to a cut-off mode and decouples the battery 36 from the rest of the threshold detection circuit 26. This off condition continues until the switch S1 is pushed again.

The automatic turn-off circuit 48 supplies power to the threshold detection circuit 26 for about seven minutes after the push button switch S1 is pressed, which should give ample time for people to use the calibrator 12 to calibrate their audio system. The automatic turn-off circuit 48 then turns power off, thereby preserving the life of the battery 36. Also, the quiescent current of the off state of the automatic turn-off circuit 48 is on the order of a few microamps, which also contributes to long battery life.

One skilled in the art will recognize that all or part of the threshold detection circuit 26 could be implemented in other ways and still allow for proper calibration. For example, a full wave rectifier could be employed. Also, a NOR gate could be employed in place of the transistors Q3 and Q4 in the window comparator 46, or the entire window comparator could be replaced with a single comparator which compares the electrical signal amplitude to a reference level designed to correspond to the value of the calibration tone's decibel level, the comparator turning on an indicator whenever the signal matches the reference level to within the tolerance of the comparator. Alternatively, voltage controlled oscillators could be employed to convert the voltage level of the electrical signal to a given frequency, which could then be compared to frequency based reference levels.

As a further alternative, digital circuits may be used. For example, the electrical signal output by the microphone could be converted into a digital signal by an analog-to-digital converter, and the digital signal could be processed by a microcontroller or microprocessor to determine the amplitude of the sound and compare it to desired reference value(s) retrieved from a look-up table stored in a memory device.

The calibrator 12 is used to calibrate an audio system as follows. The end cap 22 is removed from the housing 18 and the conventional 9 volt battery 36 is inserted into the cavity 34 and into electrical contact with the threshold detection circuitry 26. The end cap 22 is then replaced tightly onto the housing 18. The switch S1 is pressed to activate the threshold detection circuit 26. When first activated, the yellow LED 28 lights up, indicating the lack of significant background noise which could adversely affect proper calibration. If the calibrator is functioning properly, loud noises such as claps should momentarily activate the red LED.

The CD 14 is then placed into the CD player, the jack of headphones 2 are inserted into the CD player, and any speakers connected to the CD player are turned off. Because the 1000 Hz, 77 dB SPL calibration tone is prerecorded on the CD 14 so as to only be heard in the right channel and through the right earpiece 4 of the headphones 2, the earpieces of the headphones 2 are placed on the calibrator with the right earpiece 4 in contact with the end cap 20 having the microphone 24 recessed therein and the left earpiece 5 in contact with the opposite end cap 22. The adapter disk 16 is used as necessary for large headphones with cup earpieces, and the band 39 is used as necessary to retain earbuds 8 in contact with the end caps 20, 22.

The calibrator 12 and headphone 2 assembly is placed on a soft surface such as a towel to provide cushioning and prevent vibration noises from interfering with the calibration. Track 2 of the CD, containing the calibration tone, is then played, and the volume of the CD player is adjusted up and down until the green LED 30 is lit. The yellow LED 28 and red LED 32 indicate whether the volume is too low or too loud, respectively, and the volume is adjusted accordingly. Once the green LED 30 is lit, the audio system is properly calibrated and the volume is left at its current setting for the entire hearing test.

The headphones 2 are then removed from the calibrator 12 and placed on the test subject's head for testing one ear. The headphones are then reversed on the subject's head for testing the other ear.

The prerecorded contents of the CD 14 of one preferred embodiment and the method of using the CD to take a hearing test are now described with reference to FIGS. 9A–9C. As described above, track 2 of the CD contains the prerecorded calibration tone. Other tracks on the CD contain prerecorded sequences of 500-ms tones (500-ms interonset-interval), presented monaurally at each of a number of stimulus levels. For use with a first, broader phase of testing, decibel levels in one sequence of tones begin at 70 dB HL and descend in 10 dB steps to 0 dB HL. See FIG. 9A. The range of 70 dB HL to 0 dB HL was chosen for the preferred embodiments to test for hearing loss in elderly persons, who exhibit moderate hearing loss in the 40–60 dB HL range. Other ranges may be used as appropriate to test for hearing in different applications, for example, to test for acute hearing abilities in the range of −10 dB HL or −15 dB HL.

Each decibel level in the sequence is generally represented by a series of tones recorded at five different frequencies—250 Hz, 500 Hz, 1000 Hz, 2000 Hz, and 4000 Hz. Although some audiograms include octave frequencies ranging from 125 Hz to 8000 Hz, the 250–4000 Hz range of frequencies was selected for the home hearing test system 10 of preferred embodiments of the present invention for several reasons. First, many commercially available consumer headphones do not adequately represent high frequencies, so 4000 Hz was selected as the highest frequency. Frequencies below 250 Hz present a problem for at least two reasons. First, the digital range of levels is reduced for lower frequencies due to the shape of the normal audiogram. Second, ambient noise in the home will be more likely to have low frequencies due to motors, etc., which may interfere with the validity of the test. Therefore, 250 Hz, with a digital range of 50 dB, was the lowest frequency selected for testing in the preferred embodiment.

Also, although the 16 bit digital resolution used on CD quality recordings has theoretically a 93 dB digital recording range, the inventors have found that at the lowest digital levels sine wave (pure tone) signals are not properly preserved by the analogue-to-digital hardware on output. That is, a sine wave generated at one frequency is distorted on output thereby representing multiple frequencies. Thus the digital range for recordings on the CD 14 is restricted to 70 dB such that sine waves would be maintained on audio output as pure tones.

Figure 9C:
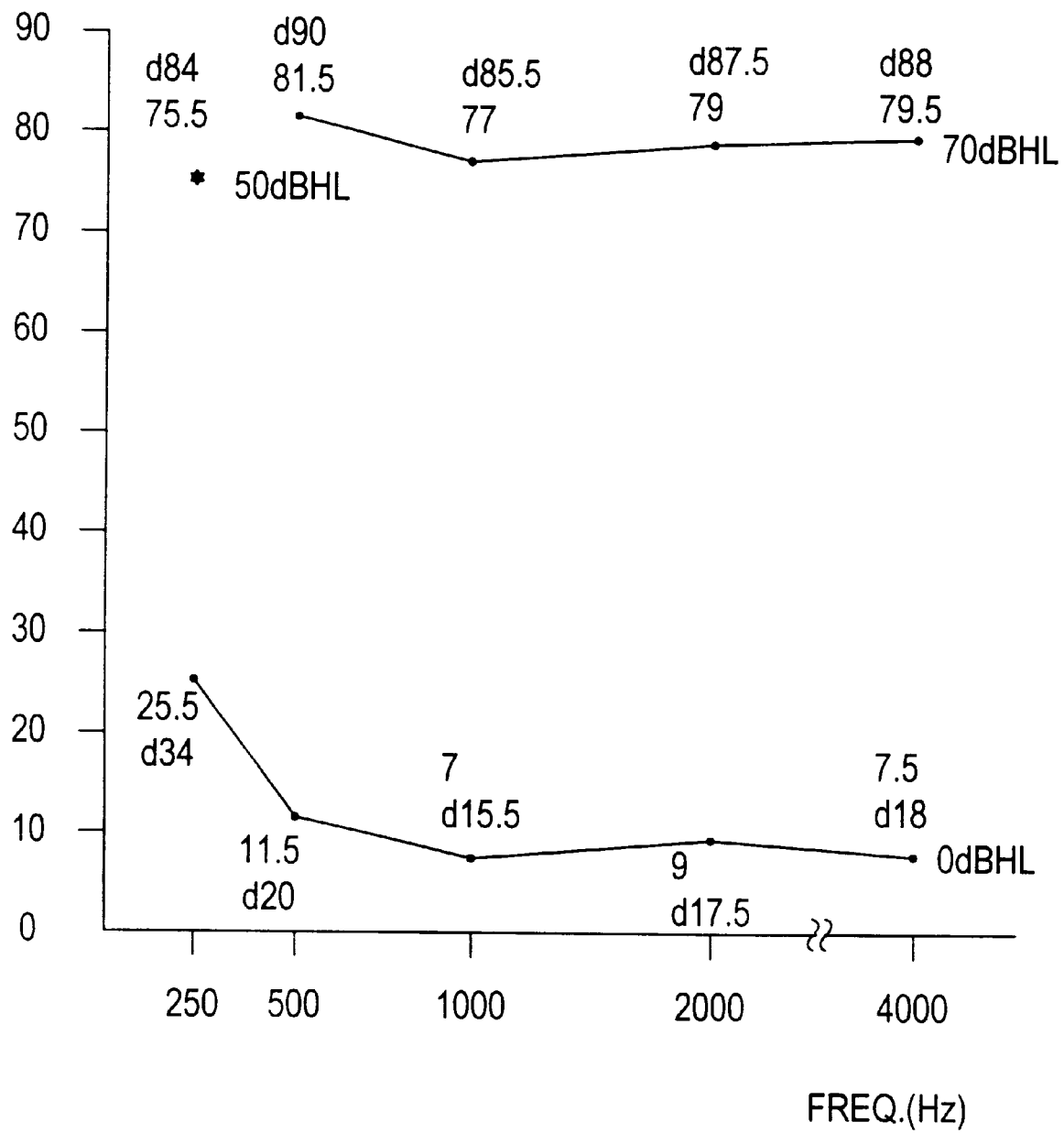
FIG. 9C is a graph of the Sound Pressure Levels for tones at 0 dB HL and 70 dB HL for different frequencies of tones recorded on the CD.

FIG. 9A shows the decibel levels in SPL and the digital levels (represented as Dx, with x being the digital recording level) which correspond to the decibel levels in HL for each frequency. Thus, for example, to produce a 50 dB HL tone at 1000 Hz, a tone of 57 dB SPL is recorded on the CD at a digital level of 65.5. FIG. 9C is a graph representing the decibel levels of tones in the first sequence in dB SPL versus the five frequencies for the 70 dB HL and 0 dB HL tones.

One skilled in the art will recognize that a broader range of test frequencies may be provided on the CD for use with specified headphones having a greater range. Also, different test frequency ranges may be employed with a modified calibration procedure wherein a number of calibration tones at different dB audio levels are recorded on the CD. The selection of a lower or weaker tone of two calibration tones when calibrating the headphones raises the dynamic range of the entire hearing test by approximately the difference in dB between the two calibration tones. Thus, if a person calibrates the headphones using a stronger calibration tone and can not hear even the strongest tones in the test, the level of the entire test could be raised by recalibrating the headphones using the weaker calibration tone. Recording a series of calibration tones on the CD provides a range of possible tests without having to record additional sequences of tones.

Each tone at a given level is introduced on the CD by a voice announcing the stimulus level (e.g., "70 decibels"). The use of predictable tone presentation times and announcements of the decibel levels to stimulus presentation allow trials to be defined for scoring purposes. The announcement at the start of each trial lets the subject know when each trial begins and ends.

At each decibel level, test subjects indicate on an answer sheet whether they heard all of the tones, some of the tones, or none of the tones. Each tone at a given level is followed by 5 seconds of silence to allow subjects time for responding.

Once all frequencies at all decibel levels in the first phase have been tested with one ear, test subjects are instructed on the CD to reverse the headphones and replay the track containing the first phase of tones to test the second ear in the same manner. When both ears have been tested, subjects are told on the CD how to obtain a preliminary threshold estimate prior to continuing with the second phase of the testing in which a more precise estimate is obtained. In one embodiment, thresholds are computed by taking the average of the lowest level at which all tones were heard and the highest level at which no tones were heard.

For the second phase of testing, the CD 14 contains multiple sequences of tones recorded on separate tracks and having decibel levels starting from one of the decibel levels in the first phase, ending with another decibel level in the first phase, and decreasing in decibel level from the starting tone to the ending tone in 2-dB steps. For example, as shown in FIG. 9B, one track on the CD contains a prerecorded sequence of tones ranging from 60 dB HL to 40 dB HL and decreasing in 2 dB steps. As with FIG. 9A, the decibel levels in SPL and the digital levels for each tone are provided in the table in FIG. 9B. Other tracks contain sequences ranging from 50 dB HL to 40 dB HL, 40 dB HL to 30 dB HL, etc.

The threshold estimate obtained in the first phase is used to determine the starting point for a descending sequence of 2-dB steps. Subjects locate the correct starting point on the CD by consulting a look-up table that lists the appropriate track numbers for each computed threshold. Once the correct track is identified, testing continues and a new threshold is computed following the same procedures as in the first phase of testing when 10-dB steps were used.

In alternative embodiments, subjects descend in 10-dB steps until they first hear no tones. After each step they are told on the CD which track to go to (in the 2-dB-step section) if they heard no tones at the current level. They then switch tracks, continue with testing 2-dB steps, and stop at the first level at which they hear no tones. The threshold will be defined as the level at which they last heard some of the tones. This procedure produces similar results to the procedure described above while simplifying the task involved in marking an answer sheet and consulting a look-up table to determine which track to switch to based on tone thresholds heard and/or not heard in the first phase.

As described above, the tones of different frequency are recorded and presented at each decibel level with predictable isochronous timing. In addition to providing multiple observation opportunities, this lets test subjects know when tones will be presented. Both reduction of temporal uncertainty and multiple observation intervals have the potential to lower thresholds by 2 or 3 dB. Furthermore, multiple observations should reduce the effects of occasional background noise, and the temporal regularity should facilitate attentional focusing while making it easier for subjects to follow the sequence of events during testing.

As one skilled in the art will recognize, other types of hearing tests may be included on the CD 14, including screening tests consisting of a broad range of tones at a single frequency or speech tests consisting of spoken words. In addition, when a computer readable medium such as a CD-ROM is used to store the hearing test, one skilled in the art will recognize that the medium may contain computer programs which cause to be displayed on the computer's monitor the instructions, announcements and look-up table used during the hearing test, or which automatically determine the subject's initial hearing threshold level estimation based on the results of the 10 dB step sequences and automatically transfer the subject to the appropriate 2 dB step sequence to obtain the more accurate results. This would potentially further simplify the testing procedure.

One skilled in the art will also recognize that other sound reproduction equipment may be used instead of the headphones, possibly with varying results. For example, a standard set of speakers connected to the output of the audio system may be used for the test, and may be calibrated by placing the calibrator 12 in the same location relative to the speakers as the location the person will occupy during the hearing test. Headphones are preferable to speakers in certain conditions in order to help minimize background noise which could affect the accuracy of the calibration and hearing test.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

What is claimed is:

1. A home hearing test system for use with an audio system, the audio system including an audio player and a sound reproducer connected to the audio player, the home hearing test system comprising:

an audio medium containing signals recorded thereon, the signals being playable by the audio player, the signals comprising at least one calibration tone recorded at a predetermined decibel level and one or more prerecorded sequences of tones, each sequence having tones at different decibel levels; and a calibration device for calibrating the output of the audio system, the calibration device measuring sound output by the sound reproducer, the calibration device further comparing the measured sound to the predetermined decibel level of the calibration tone.

2. The system of claim 1 wherein the audio medium comprises a digital audio medium.

3. The system of claim 2 wherein the audio medium comprises a CD.

4. The system of claim 2 wherein the audio medium comprises a CD-ROM and the audio player comprises a CD-ROM player and sound card connected to a personal computer.

5. The system of claim 2 wherein the audio medium is located at a server computer on a network and wherein the audio player comprises a client computer connected to the network for receiving the signals stored on the audio medium over the network.

6. The system of claim 1 wherein a plurality of the tones recorded in each sequence on the audio medium are recorded at the same decibel level but at different frequencies.

7. The system of claim 6 wherein the frequencies of the tones vary between 250 Hz and 4000 Hz, inclusive.

8. The system of claim 1 wherein the signals comprise a first sequence of tones in which the decibel levels of the tones decrease or increase by a first step value and a second sequence of tones in which the decibel levels of the tones decrease or increase by a second step value, the first step value being different than the second step value.

9. The system of claim 8 wherein the first step value is 10 dB and the second step value is 2 dB.

10. The system of claim 9 wherein the first sequence begins at 70 dB HL and decreases to 0 dB HL.

11. The system of claim 8 wherein the audio medium is a CD having a plurality of tracks, and wherein the first sequence is recorded in a first track on the CD and the second sequence is recorded in a second track on the CD.

12. The system of claim 8 wherein the signals comprise a plurality of sequences of tones which decrease by the second step value, each of which begins at a starting tone having a decibel level equal to the decibel level of one of the tones in the first sequence and ends at an ending tone having a decibel level equal to the decibel level of another of the tones in the first sequence.

13. The system of claim 1 wherein the signals comprise a plurality of calibration tones at different decibel levels.

14. The system of claim 1 wherein the calibration device comprises:

at least one transducer for detecting sound being output by the sound reproducer and converting the detected sound into an electrical signal having at least one parameter related to the decibel level of the detected sound;

a first circuit coupled to the transducer and having an output related to the relationship between the at least one parameter of the electrical signal and at least one reference level related to the predetermined decibel level of the calibration tone; and at least one indicator coupled to an output of the first circuit for indicating the relationship between the electrical signal and the at least one reference level.

15. The system of claim 14 wherein the calibration device further comprises a high pass filter circuit coupled to the transducer for minimizing the presence of low frequencies in the electrical signal to thereby minimize background noise present while the system is being used to test a person's hearing.

16. The system of claim 14 wherein the first circuit comprises a reference circuit for producing the at least one reference voltage and a comparator circuit coupled to receive the electrical signal and the at least one reference level.

17. The system of claim 16 wherein the calibration device calibrates the audio system to within a window of accuracy, wherein the reference circuit produces a first reference level corresponding to a high end of the window of accuracy and a second reference level corresponding to a low end of the window of accuracy, and wherein the comparator circuit compares the electrical signal to the first and second reference levels to thereby detect when the electrical signal is between the first and second reference levels.

18. A home hearing test system for use with an audio system, the audio system including an audio player and a sound reproducer connected to the audio player, wherein the sound reproducer is a set of headphones, the home hearing test system comprising:
    an audio medium containing signals recorded thereon, the signals being playable by the audio player, the signals comprising at least one calibration tone recorded at a predetermined decibel level and one or more prerecorded sequences of tones, each sequence having tones at different decibel levels;
    a calibration device for calibrating the output of the audio system, the calibration device measuring sound output by the sound reproducer, the calibration device further comparing the measured sound to the predetermined decibel level of the calibration tone; and
    means for providing a first level of contact pressure between the calibration device and at least one earpiece of the headphones which is substantially equal to a second level of contact pressure between the earpiece and an ear when the headphones are worn by a person.

19. The system of claim 18 wherein the means comprises a housing for the calibration device having a length approximately equal to the width of an average human head.

20. A home hearing test system for use with an audio system, the audio system including an audio player and a sound reproducer connected to the audio player, wherein the sound reproducer is a set of headphones, the home hearing test system comprising:
    an audio medium containing signals recorded thereon, the signals being playable by the audio player, the signals comprising at least one calibration tone recorded at a predetermined decibel level and one or more prerecorded sequences of tones, each sequence having tones at different decibel levels;
    a calibration device for calibrating the output of the audio system, the calibration device measuring sound output by the sound reproducer, the calibration device further comparing the measured sound to the predetermined decibel level of the calibration tone; and
    an earpiece adapter plate releasably connectable to an end of the calibration device and having a surface area substantially commensurate with a surface area of an earpiece of a conventional set of large headphones.

21. A method for testing a person's hearing at the person's home using an audio player, a sound reproducer connected to the audio player, and an audio medium playable in the audio player, the method comprising:
    calibrating the output of the sound reproducer against a calibration tone of a predetermined decibel level prerecorded on the audio medium;
    listening through the sound reproducer to a first sequence of tones prerecorded on the audio medium, the first sequence comprising a plurality of tones recorded at decibel levels which decrease or increase;
    indicating which of the tones in the first sequence were heard and/or not heard.

22. The method of claim 21, further comprising, based on tones in the first sequence indicated to have been heard and/or not heard, selecting and listening to a second sequence of tones prerecorded on the audio medium, the second sequence having a plurality of tones recorded at different decibel levels ranging between a first tone in the first sequence which was not heard and a second tone in the first sequence which was heard.

23. The method of claim 22, wherein the tones in the first sequence increase or decrease by a first step value and the tones in the second sequence increase or decrease between the first tone and second tone at a second step value, the second step value being smaller than the first step value.

* * * * *